United States Patent [19]

Sundt et al.

[11] 4,387,047
[45] Jun. 7, 1983

[54] ESTERS OF 1,3-DIMETHYL-BUT-3-EN-1-YL, THEIR UTILIZATION AS PERFUMING AND FLAVORING INGREDIENTS AND COMPOSITIONS CONTAINING SAME

[75] Inventors: Erling Sundt, Vessy/Ge; Walter Schenk; Roger Chappaz, both of Geneva; Michel Joyeux, Petit-Lancy/Ge, all of Switzerland

[73] Assignee: Firmenich SA, Geneva, Switzerland

[21] Appl. No.: 223,013

[22] Filed: Jan. 6, 1981

[30] Foreign Application Priority Data

Feb. 13, 1980 [CH]  Switzerland ................. 1162/80

[51] Int. Cl.³ .................. A61K 7/46; A23L 2/26
[52] U.S. Cl. .................. 252/522 R; 560/113; 560/261; 560/225; 426/534; 426/538; 252/174.11
[58] Field of Search .............. 252/522 R; 560/261, 560/113, 225; 426/534, 538

[56] References Cited

U.S. PATENT DOCUMENTS 3,655,735  4/1972  Pommer et al. ............ 560/261
3,959,396  5/1976  Ochsner et al. ............ 252/522 R
3,962,344  6/1976  Ploner et al. ............ 252/522 R Primary Examiner—John F. Niebling
Attorney, Agent, or Firm—Pennie & Edmonds

[57] ABSTRACT

Use of certain ester derivatives of 1,3-dimethyl-but-3-en-1-yl as perfuming and flavoring ingredients. These ester derivatives possess the following formula

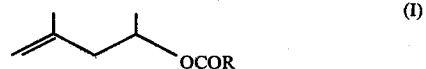
(I)

wherein symbol R represents a hydrogen atom, a saturated or an unsaturated, linear or branched lower alkyl having 1 to 6 carbon atoms, or an aryl radical. The compounds of formula (I) are new chemical entities.

15 Claims, No Drawings

ESTERS OF 1,3-DIMETHYL-BUT-3-EN-1-YL, THEIR UTILIZATION AS PERFUMING AND FLAVORING INGREDIENTS AND COMPOSITIONS CONTAINING SAME

SUMMARY OF THE INVENTION

The instant invention relates to ester derivatives of 1,3-dimethyl-but-3-en-1-yl of formula

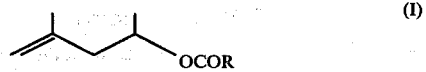

(I)

wherein symbol R represents a hydrogen atom, a saturated or an unsaturated, linear or branched lower alkyl having 1 to 6 carbon atoms, or an aryl radical.

This invention relates further to a method for imparting, improving or modifying the olfactive properties of perfumes or perfumed articles, or the gustative properties of foodstuffs, animal feeds and beverages which method comprises the step of adding thereto an organoleptic effective amount of at least one of the ester derivatives of 1,3-dimethyl-but-3-en-1-yl of formula (I).

A further object of the present invention consists in a perfuming or flavouring composition containing as effective ingredient an ester derivative of formula (I).

A still further object of the invention consists in a perfumed article containing as perfuming effective ingredient an ester derivative of formula (I).

BACKGROUND OF THE INVENTION

Among the variety of synthetic compounds presently at the disposal of perfumers and flavorists, there appear to be several ester derivatives of aliphatic carboxylic acids and lower aliphatic alcohols.

In order to further enlarge the choice of available ingredients and thus enable the creation of novel and original odorous or gustative notes, we have realized the synthesis of a series of new compounds. These are ester derivatives of 1,3-dimethyl-but-3-en-1-ol, viz. carboxylic esters of 1,3-dimethyl-but-3-en-1-yl. We have unexpectedly discovered that the said compounds possess useful perfuming and flavoring characters and consequently they can be advantageously used in the perfume and flavor industry.

PREFERRED EMBODIMENTS OF THE INVENTION

The ester derivatives of the instant invention develop various notes of green, flowery or even fruity type. The fragrance developed by some of them is reminiscent of that possessed by camomile, especially of its top notes. Owing to their odorous properties, compounds (I) can be used in combination with a great variety of other current perfuming ingredients, diluents or carriers.

In the field of perfumery, the proportions at which the said compounds can achieve interesting perfuming effects can vary within wide limits depending on the nature of the perfumed article or the specific effect it is desired to achieve. These proportions can preferably be of the order of 5 to 20% by weight, based on the total weight of the composition in which they are incorporated. These values, however, should not be interpreted restrictively and it should be understood by those skilled in the art that concentrations lower or higher than those indicated above may be used in practice. For instance, in applications destined to perfume house-hold materials, detergents, cosmetics or toilet soaps, concentrations of the order of 0.1 to 0.5% by weight can already be considered as sufficient.

In the field of flavors, compounds (I) develop gustative notes of herbal, flowery, rosy, resinous and fruity type, which notes are reminiscent of camomile.

A special interest is presented by propionic, isobutyric and tiglic esters.

For aromatization purposes, the compounds of the invention can be used in various concentrations. Proportions of the order of about 1 to 50 ppm (parts per million), more particularly of about 10 ppm based on the total weight of the flavored materials into which compounds (I) are added, can achieve satisfactory results. Among the compounds of formula (I), 1,3-dimethyl-but-3-en-1-yl salicylate is a flavor ingredient of particular utility; it possesses good strength and typically it can be used at concentrations of 0.1 to 0.5 ppm.

The esters of the invention can be utilized in their isolated form or more frequently in admixture with other perfuming or flavoring ingredients, in solution or over a support or a carrier.

As indicated above, symbol R can represent a saturated or unsaturated, linear of branched lower alkyl radical having 1 to 6 carbon atoms or an aryl radical.

Thus symbol R can stand e.g. for methyl, ethyl, propyl, isopropyl, butyl, isobutyl, tert-butyl or pentyl, or an alkenyl radical such as 1-methyl-prop-1-en-1-yl. R can also represent a substituted or unsubstituted aryl radical, for instance phenyl or o-hydroxy-phenyl.

Typical compounds of formula (I) in accordance with the invention include the following:
   1,3-dimethyl-but-3-en-1-yl formate,
   1,3-dimethyl-but-3-en-1-yl acetate,
   1,3-dimethyl-but-3-en-1-yl propionate,
   1,3-dimethyl-but-3-en-1-yl butyrate,
   1,3-dimethyl-but-3-en-1-yl isobutyrate,
   1,3-dimethyl-but-3-en-1-yl isovalerianate,
   1,3-dimethyl-but-3-en-1-yl tiglate,
   1,3-dimethyl-but-3-en-1-yl benzoate,
   1,3-dimethyl-but-3-en-1-yl salicylate.

A special interest is presented by isobutyrate, tiglate, benzoate and salicylate.

Esters (I) can be prepared starting from 1,3-dimethyl-but-3-en-1-ol according to current methods. The following examples summarize their preparation.

Propionic, butyric and isobutyric esters 0.2 Moles of the appropriate acid chloride (propionyl, butyral or isobutyryl chloride) were added dropwise to a mixture kept at 0°/+5° of 1,3-dimethyl-but-3-en-1-ol (0.2 M) and diethylaniline (0.22 M).

Once the addition was over, the reaction mixture was stirred at room temperature during 2 h while adding 50 ml of isopropyl ether followed by 0.04 M of the chosen acid chloride.

The resulting mixture is then heated for 2 h at 40°–50° and kept overnight under stirring at room temperature, then cooled to about 5°. 50 ml of 5% sulfuric acid were then added to the mixture and the organic phase was washed once with water, twice with a 10% aqueous solution of sodium carbonate and twice with brine. The organic phase was then dried over $Na_2SO_4$, concentrated and distilled to yield the desired ester.

propionic ester:
   yield 70%; b.p. 59°/$1.73.10^3$ Pascal.
   MS: m/e=57, 82, 29, 67, 41, 101, 112, 141, 119.

butyric ester:
yield about 70%; b.p. 75°/1.73.10³ Pascal.
MS: m/e=71, 43, 82, 55, 27, 115, 89, 126, 141, 155, 105.

isobutyric ester:
yield about 70%; b.p. 60°/1.33.10³ Pascal.
MS: m/e=71, 43, 82, 55, 27, 115, 126, 155.

Acetic acid ester

A mixture of 0.2 M of 1,3-dimethyl-but-3-en-1-ol, 0.2 M of acetic anhydride and 0.5 g of p-toluenesulfonic acid was stirred while the temperature increased from 20° to 50°-60°. 0.04 Moles of acetic anhydride were then added to the reaction mixture in order to complete the reaction and the whole was kept at 50° for 1 h. After cooling, 50 ml of isopropyl ether and 50 ml of ice-water were added to the mixture and the organic phase was separated, washed twice with water, with an aqueous solution of sodium bicarbonate and finally with water again until neutrality, then dried over $Na_2SO_4$. The desired ester was obtained by fractional distillation by means of a Fischer type column of 40 cm length.

Yield about 35%; b.p. 43°/1.73.10³ Pascal.
MS: m/e=43, 82, 67, 55, 27, 98, 127, 109, 143.

Formic acid ester 46 g (1 M) of formic acid were added dropwise under vigorous stirring to 50 g (0.5 M) of 1,3-dimethyl-but-3-en-1-ol and the obtained mixture was kept standing for 2 h at room temperature, then at 60° for 4 h. The reaction mixture was then diluted with pentane and the organic phase was washed twice with water, with an aqueous solution of sodium bicarbonate and with water again until neutrality. After filtration over a column of $SiO_2$ and evaporation, the obtained residue was distilled under reduced pressure by means of a Widmer type apparatus to give 17.7 g of the desired product.

B.p. 110°/9.71.10⁴ Pascal.
NMR: 1.22 and 1.33 (3H, 2s); 1.78 (3H, s); 2.3 (2H, q); 4.78–5.25 (3H, m); 8.0 (1H, m) δ ppm.

Isovalerianic acid ester 20.9 g of isovalerianyl chloride (0.2 M) were added under stirring within 45 min. to a solution of 20 g (0.2 M) of 1,3-dimethyl-but-3-en-1-ol in 60 ml of anhydrous diethyl ether and 23.7 g (0.3 M) of anhydrous pyridine.

The mixture was then kept at reflux for 1 h, then cooled to room temperature, whereupon 100 ml of ice-water were added thereto.

An extraction with ether (2x) followed by the usual treatment of acidification, washing and neutralization of the organic extracts, gave a clear solution which upon evaporation and distillation yielded the desired ester having b.p. 71°/1.33.10³ Pascal (yield 66.8%).

MS: m/e=129, 103, 85, 82, 67, 57, 41, 29.
NMR: 0.83 and 0.95 (6H, 2s); 1.10 and 1.21 (3H, 2s); 1.70 (3H, 1s); 2.12 (5H, m); 4.70 (2H, m); 5.05 (1H, q) δ ppm.

Tiglic acid ester (3-methyl-trans-but-2-enoic)

13.5 g (0.113 M) of 3-methyl-trans-but-2-enoyl chloride have been added within 5 minutes to a solution of 10 g (0.1 M) of 1,3-dimethyl-but-3-en-1-ol in 115 ml of anhydrous toluene. The reaction mixture was then heated to reflux for 3½ h and, after cooling, was mixed with 45 ml of a saturated aqueous solution of $NaHCO_3$, whereupon it was stirred at room temperature for 30 minutes.

The separated organic phase was subjected to the usual treatment of washing and neutralization and the volatile parts were evaporated. The thus obtained residue was fractionally distilled twice using a Vigreux and a Fischer type column, respectively, to give the desired product having b.p. 85°/1.33.10³ Pascal; yield 44%.

MS: m/e=127, 101, 83, 82, 67, 55, 39, 29.
NMR: 1.18 and 1.28 (3H, d); 1.72–1.80 (9H); 2.20–2.36 (2H); 4.70 (2H, s); 4.92–5.25 (1H, q); 6.80 (1H, m) δ ppm.

Benzoic acid ester

This ester was prepared as described above for the ester derivative of isovalerianic acid by making use of 20.0 g (0.2 M) of 1,3-dimethyl-but-3-en-1-ol, 28.1 g (0.2 M) of benzoyl chloride and 27.7 g (0.3 M) of dry pyridine.

There were thus obtained 27.8 g of the desired ester having b.p. 122°/1.33.10³ Pascal.

MS: m/e=105, 82, 77, 67, 51, 41, 27.
IR: 3100, 3000, 1710, 1640, 1445, 1270, 1100, 895, 700 cm⁻¹.
NMR: 1.20–1.30 (3H, 2s); 1.69 (3H, 1s); 2.30 (2H, q); 4.70 (2H, s); 5.25 (1H, q); 7.40 (3H, m); 7.85 (2H, m) δ ppm.

Salicylic acid ester

This ester was prepared as indicated above for the ester derivative of isovalerianic acid by making use of 1.0 kg (10 M) of 1,3-dimethyl-but-3-en-1-ol and salicyl chloride obtained by chloridation of 1.380 kg (10 M) of salicylic acid with 1.190 kg (10 M) of thionyl chloride in the presence of pyridine.

1,3-Dimethyl-but-3-en-1-yl salicylate (1.520 kg) thus obtained had b.p. 110°/1.33 Pascal; yield 69%.

NMR: 1.3 and 1.4 (4H, 2s); 1.60 (1H, 1d); 1.76 (3H, 1s); 2.37 (2H, q); 3.78 (2H, s); 5.35 (1H, q); 6.8–7.87 (4H, m) δ ppm.

We have observed that the corresponding saturated esters, viz. the ester derivatives of 1,3-dimethyl-butyl, possesses also interesting organoleptic properties, though less pronounced. These esters can be obtained starting from 1,3-dimethyl-butanol according to the usual techniques of esterification.

1,3-Dimethyl-but-3-en-1-ol, used as starting material in the above described procedure, can be obtained according to known methods, e.g. in accordance with the process described in Japanese Application No. 76 70708 [see Chem. Abstr. 85, 123 338 d (1976)].

The temperatures given above are indicated in degrees centigrade and the abbreviations have the meaning common in the art.

The invention is better illustrated by but not limited to the following examples.

EXAMPLE 1

The esters prepared as indicated above have been subjected to an olfactive evaluation by a panel of perfumers. The following table summarizes the results of such an evaluation.

| 1,3-Dimethyl-but-3-en-1-yl ester | Olfactive evaluation |
|---|---|
| formate | fugaceous, green |
| acetate | fugaceous, green-fruity |
| propionate | green, flowery-fruity |
| butyrate | flowery-fruity |
| isobutyrate | excellent flowery and fruity |

| 1,3-Dimethyl-but-3-en-l-yl ester | Olfactive evaluation |
|---|---|
| | note reminiscent of the top note of camomile |
| isovalerianate | flowery-fruity |
| tiglate | good flowery-fruity note reminiscent of certain aspects of camomile |
| benzoate | flowery, green |
| salicylate | flowery, green |

EXAMPLE 2

A base perfume composition of flowery and fruity type was obtained by mixing the following ingredients (parts by weight):

| | |
|---|---|
| phenyl ethanol | 100 |
| cis-hex-3-enyl-salicylate | 80 |
| trimethylhexyl acetate | 80 |
| benzyl acetate | 80 |
| linalol | 60 |
| heliotropine | 50 |
| hydroxycitronellol | 50 |
| citronellyl acetate | 40 |
| levo-citronellol | 40 |
| undecylenic aldehyde 10%* | 40 |
| 1,1-dimethyl-4-acetyl-6-tert-butyl-indane | 30 |
| α-amylcinnamic aldehyde | 30 |
| α-isomethyl ionone | 30 |
| α-damascone 10%* | 20 |
| styrallyl acetate | 20 |
| 4-isopropyl-cyclohexyl-methanol | 10 |
| amyl salicylate | 20 |
| allyl caproate 10%* | 20 |
| Hedione[1]® | 10 |
| anisaldehyde | 5 |
| β-damascenone 1%* | 5 |
| α-methyl-p-tert-butyl-hydro-cinnamaldehyde | 20 |
| Total | 840 |

*in diethyl phthalate
[1]Origin: Firmenich SA, Geneve, Suisse

By adding to 84 g of the above base 6 g of 1,3-dimethyl-but-3-en-1-yl benzoate, one obtains a novel composition having an olfactive character of flowery, herbaceous and aromatic type whereas the predominant note of the base was fruity.

By adding to the thus obtained novel composition 10 g of 1,3-dimethyl-but-3-en-1-yl isobutyrate, there was obtained a novel composition of camomile type. Such a composition was perfectly adapted to the perfuming of articles destined to hair treatment, for instance shampoos.

EXAMPLE 3

The compounds prepared in accordance with the methods described above were subject to a gustative evaluation by a panel of flavor experts. The following table summarizes such an evaluation.

| 1,3-Dimethyl-but-3-en-l-yl ester | Gustative evaluation |
|---|---|
| acetate | earthy, slightly herbal and fruity |
| propionate | herbal, camomile, slightly flowery-rosy |
| butyrate | fatty |
| isobutyrate | herbal, resinous |
| isovalerianate | fruity |
| tiglate | herbal, resinous |
| benzoate | slightly flowery |
| salicylate | flowery |

The compounds under examination were evaluated in crystal spring water at an average concentration of 10 ppm (parts per million) by weight with the exception of the salicylate which was evaluated at 0.3 ppm.

What we claim is:

1. 1,3-Dimethyl-but-3-en-1-yl formate.
2. 1,3-Dimethyl-but-3-en-1-yl acetate.
3. 1,3-Dimethyl-but-3-en-1-yl propionate.
4. 1,3-Dimethyl-but-3-en-1-yl butyrate.
5. 1,3-Dimethyl-but-3-en-1-yl isobutyrate.
6. 1,3-Dimethyl-but-3-en-1-yl isovalerianate.
7. 1,3-Dimethyl-but-3-en-1-yl tiglate.
8. 1,3-Dimethyl-but-3-en-1-yl benzoate.
9. 1,3-Dimethyl-but-3-en-1-yl salicylate.
10. A method for imparting or modifying the olfactive properties of perfumes or perfumed articles, or the gustative properties of foodstuffs, animal feeds and beverages which comprises the step of adding thereto an olfactive amount of at least one of the ester derivatives of a compound of formula

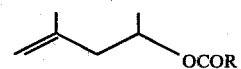

wherein symbol R represents a hydrogen atom, a saturated or unsaturated, linear or branched lower alkyl having 1 to 6 carbon atoms, or an aryl radical.

11. A perfuming or flavoring composition containing as effective ingredient an ester derivative of formula

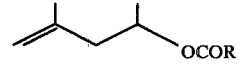

wherein symbol R represents a hydrogen atom, a saturated or an unsaturated, linear or branched lower alkyl having 1 to 6 carbon atoms, or an aryl radical.

12. A perfumed article containing as perfuming effective ingredient an ester derivative of formula

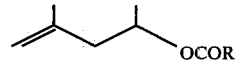

wherein symbol R represents a hydrogen atom, a saturated or an unsaturated, linear or branched lower alkyl having 1 to 6 carbon atoms, or an aryl radical.

13. A method for imparting, improving or modifying the olfactive properties of perfumes or perfumed articles, or the gustative properties of foodstuffs, animal feeds and beverages which comprises the step of adding thereto an olfactive amount of 1,3-dimethyl-but-3-en-1-yl isobutyrate.

14. A perfuming or flavoring composition containing as effective ingredient 1,3-dimethyl-but-3-en-1-yl isobutyrate.

15. A perfumed article containing as perfuming effective ingredient 1,3-dimethyl-but-3-en-1-yl isobutyrate.

* * * * *